(12) United States Patent
Hartwell (10) Patent No.: US 8,764,732 B2
(45) Date of Patent: Jul. 1, 2014

(54) WOUND DRESSING

(75) Inventor: Edward Yerbury Hartwell, Hull (GB)

(73) Assignee: Smith & Nephew PLC, London (GB)

( * ) Notice: Subject to any disclaimer, the term of this patent is extended or adjusted under 35 U.S.C. 154(b) by 208 days.

(21) Appl. No.: 12/744,277

(22) PCT Filed: Nov. 20, 2008

(86) PCT No.: PCT/GB2008/051090
§ 371 (c)(1),
(2), (4) Date: Sep. 20, 2010

(87) PCT Pub. No.: WO2009/066106
PCT Pub. Date: May 28, 2009

(65) Prior Publication Data
US 2011/0028918 A1    Feb. 3, 2011

(30) Foreign Application Priority Data

Nov. 21, 2007  (GB) .................................. 0722820.8
Sep. 17, 2008  (GB) .................................. 0817020.1

(51) Int. Cl.
*A61M 27/00*     (2006.01)
*A61F 13/00*     (2006.01)

(52) U.S. Cl.
CPC .......... *A61M 27/00* (2013.01); *A61F 13/00068* (2013.01)
USPC ............................ 604/543; 604/317; 604/319

(58) Field of Classification Search
CPC ................ A61M 27/00; A61M 1/0088; A61F 13/00068; A61F 13/0216
USPC .................. 604/540, 543, 317–327
See application file for complete search history.

(56) References Cited

U.S. PATENT DOCUMENTS

| 695,270 | A | 3/1902 | Beringer |
| 1,480,562 | A | 1/1924 | Mock |
| 2,280,915 | A | 4/1942 | Johnson |
| 2,367,690 | A | 7/1943 | Purdy |
| 2,568,933 | A | 9/1951 | Robbins |
| 2,632,443 | A | 3/1953 | Lesher |
| 2,682,873 | A | 7/1954 | Evans et al. |

(Continued)

FOREIGN PATENT DOCUMENTS

| DE | 847475 C | 8/1952 |
| DE | 3032092 A1 | 8/1980 |

(Continued)

OTHER PUBLICATIONS

Achterberg, V., Ph.D., Hydroactive dressings and serum proteins: an in vitro study, Journal of Wound Care, February, vol. 5, No. 2, 1996 (pp. 79-82).

(Continued)

*Primary Examiner* — Philip R Wiest
*Assistant Examiner* — Benjamin Klein
(74) *Attorney, Agent, or Firm* — Knobbe Martens Olson & Bear LLP (57) ABSTRACT

A method and apparatus are disclosed for dressing a wound. The apparatus comprises an absorbent layer for absorbing wound exudate, a liquid impermeable, gas permeable filter layer over the absorbent layer, a cover layer comprising at least one orifice and a first liquid and gas permeable transmission layer underlying the absorbent layer. The transmission layer is in fluid communication with the filter layer.

37 Claims, 4 Drawing Sheets

(56) References Cited

U.S. PATENT DOCUMENTS

| | | | |
|---|---|---|---|
| 2,910,763 | A | 8/1955 | Lauterbach |
| 3,115,138 | A | 12/1963 | McElvenny et al. |
| 3,367,332 | A | 2/1968 | Groves |
| 3,572,340 | A | 3/1971 | Lloyd et al. |
| 3,874,387 | A | 4/1975 | Barbieri |
| 3,993,080 | A | 11/1976 | Loseff |
| RE29,319 | E | 7/1977 | Nordby et al. |
| 4,102,342 | A | 7/1978 | Akiyama et al. |
| 4,112,947 | A | 9/1978 | Nehring |
| 4,136,696 | A | 1/1979 | Nehring |
| 4,184,510 | A | 1/1980 | Murry et al. |
| 4,217,894 | A | 8/1980 | Franetzki |
| 4,219,019 | A | 8/1980 | Coates |
| 4,224,945 | A | 9/1980 | Cohen |
| 4,316,466 | A | 2/1982 | Babb |
| 4,382,441 | A | 5/1983 | Svedman |
| 4,465,485 | A | 8/1984 | Kashmer et al. |
| 4,534,356 | A | 8/1985 | Papadakis |
| 4,573,965 | A | 3/1986 | Russo |
| 4,608,041 | A | 8/1986 | Nielsen |
| 4,655,766 | A | 4/1987 | Theeuwes et al. |
| 4,681,562 | A | 7/1987 | Beck et al. |
| 4,710,165 | A | 12/1987 | McNeil et al. |
| 4,778,446 | A | 10/1988 | Jensen |
| 4,792,328 | A | 12/1988 | Beck et al. |
| 4,828,546 | A | 5/1989 | McNeil et al. |
| 4,921,488 | A | 5/1990 | Maitz et al. |
| 4,936,834 | A | 6/1990 | Beck et al. |
| 4,969,880 | A | 11/1990 | Zamierowski |
| 4,972,829 | A | 11/1990 | Knerr |
| 4,994,022 | A | 2/1991 | Steffler et al. |
| 5,055,198 | A | 10/1991 | Shettigar |
| 5,056,510 | A | 10/1991 | Gilman |
| 5,073,172 | A | 12/1991 | Fell |
| 5,100,396 | A | 3/1992 | Zamierowski |
| 5,134,994 | A | 8/1992 | Say |
| 5,152,757 | A | 10/1992 | Eriksson |
| 5,167,613 | A | 12/1992 | Karami et al. |
| 5,176,663 | A | 1/1993 | Svedman et al. |
| 5,215,519 | A | 6/1993 | Shettigar |
| 5,261,893 | A | 11/1993 | Zamierowski |
| 5,266,928 | A | 11/1993 | Johnson |
| 5,279,608 | A | 1/1994 | Cherif Cheikh |
| 5,328,614 | A | 7/1994 | Matsumura |
| 5,358,494 | A | 10/1994 | Svedman |
| 5,380,280 | A | 1/1995 | Peterson |
| 5,437,651 | A | 8/1995 | Todd et al. |
| 5,445,604 | A | 8/1995 | Lang |
| 5,489,280 | A | 2/1996 | Russell |
| 5,498,338 | A | 3/1996 | Kruger et al. |
| 5,527,293 | A | 6/1996 | Zamierowski |
| 5,536,233 | A | 7/1996 | Khouri |
| 5,549,584 | A * | 8/1996 | Gross ........................... 604/313 |
| 5,624,423 | A | 4/1997 | Anjur et al. |
| 5,636,643 | A | 6/1997 | Argenta et al. |
| 5,643,189 | A | 7/1997 | Masini |
| 5,645,081 | A | 7/1997 | Argenta et al. |
| 5,662,583 | A | 9/1997 | Khouri |
| 5,676,634 | A | 10/1997 | Khouri |
| 5,678,564 | A | 10/1997 | Lawrence et al. |
| 5,695,445 | A | 12/1997 | Khouri |
| 5,701,917 | A | 12/1997 | Khouri |
| 5,733,337 | A | 3/1998 | Carr et al. |
| 5,759,570 | A | 6/1998 | Arnold |
| 5,776,098 | A | 7/1998 | Silver et al. |
| 5,785,688 | A | 7/1998 | Joshi et al. |
| 5,817,145 | A | 10/1998 | Augustine et al. |
| 5,830,496 | A | 11/1998 | Freeman |
| 5,833,646 | A | 11/1998 | Masini |
| 5,843,011 | A | 12/1998 | Lucas |
| 5,868,933 | A | 2/1999 | Patrick et al. |
| 5,876,611 | A | 3/1999 | Shettigar |
| 5,964,723 | A | 10/1999 | Augustine |
| 6,010,527 | A | 1/2000 | Augustine et al. |
| 6,013,097 | A | 1/2000 | Augustine et al. |
| 6,071,267 | A | 6/2000 | Zamierowski |
| 6,093,160 | A | 7/2000 | Augustine et al. |
| 6,103,951 | A | 8/2000 | Freeman |
| 6,110,197 | A | 8/2000 | Augustine et al. |
| 6,117,111 | A | 9/2000 | Fleischmann |
| 6,135,116 | A | 10/2000 | Vogel et al. |
| 6,142,982 | A | 11/2000 | Hunt et al. |
| 6,168,800 | B1 | 1/2001 | Dobos et al. |
| 6,176,307 | B1 | 1/2001 | Danos et al. |
| 6,225,523 | B1 | 5/2001 | Masini |
| 6,248,084 | B1 | 6/2001 | Augustine et al. |
| 6,254,567 | B1 | 7/2001 | Treu et al. |
| 6,255,552 | B1 | 7/2001 | Cummings et al. |
| 6,257,847 | B1 | 7/2001 | Silver et al. |
| 6,261,283 | B1 | 7/2001 | Morgan et al. |
| 6,267,740 | B1 | 7/2001 | Augustine et al. |
| 6,287,521 | B1 | 9/2001 | Quay et al. |
| 6,291,050 | B1 | 9/2001 | Cree et al. |
| 6,293,917 | B1 | 9/2001 | Augustine et al. |
| 6,345,623 | B1 | 2/2002 | Heaton et al. |
| 6,398,767 | B1 | 6/2002 | Fleischmann |
| 6,402,724 | B1 | 6/2002 | Smith et al. |
| 6,440,167 | B2 | 8/2002 | Shimizu |
| 6,450,773 | B1 | 9/2002 | Upton |
| 6,458,109 | B1 | 10/2002 | Henley et al. |
| 6,465,708 | B1 | 10/2002 | Augustine |
| 6,468,295 | B2 | 10/2002 | Augustine et al. |
| 6,471,685 | B1 | 10/2002 | Johnson |
| 6,471,982 | B1 | 10/2002 | Lydon et al. |
| 6,481,986 | B1 | 11/2002 | Silver et al. |
| 6,491,684 | B1 | 12/2002 | Joshi et al. |
| 6,500,112 | B1 | 12/2002 | Khouri |
| 6,547,756 | B1 | 4/2003 | Greter et al. |
| 6,553,998 | B2 | 4/2003 | Heaton et al. |
| 6,580,012 | B1 | 6/2003 | Augustine et al. |
| 6,599,262 | B1 | 7/2003 | Masini |
| 6,626,891 | B2 | 9/2003 | Ohmstede |
| 6,638,270 | B2 | 10/2003 | Johnson |
| 6,648,862 | B2 | 11/2003 | Watson |
| 6,673,028 | B1 | 1/2004 | Argenta et al. |
| 6,676,610 | B2 | 1/2004 | Morton et al. |
| 6,676,631 | B1 | 1/2004 | Greter |
| 6,685,681 | B2 | 2/2004 | Lockwood et al. |
| 6,695,823 | B1 | 2/2004 | Lina et al. |
| 6,695,824 | B2 | 2/2004 | Howard et al. |
| 6,699,213 | B1 | 3/2004 | Annis et al. |
| 6,752,794 | B2 | 6/2004 | Lockwood et al. |
| 6,755,807 | B2 | 6/2004 | Risk et al. |
| 6,764,462 | B2 | 7/2004 | Risk, Jr. et al. |
| 6,767,334 | B1 | 7/2004 | Randolph |
| 6,775,807 | B2 | 8/2004 | Lowther et al. |
| 6,800,074 | B2 | 10/2004 | Henley et al. |
| 6,808,517 | B2 | 10/2004 | Greter et al. |
| 6,814,079 | B2 | 11/2004 | Heaton et al. |
| 6,824,533 | B2 | 11/2004 | Risk, Jr. et al. |
| 6,855,135 | B2 | 2/2005 | Lockwood et al. |
| 6,856,821 | B2 | 2/2005 | Johnson |
| 6,936,037 | B2 | 8/2005 | Bubb et al. |
| 6,951,553 | B2 | 10/2005 | Bubb et al. |
| 6,960,179 | B2 | 11/2005 | Gura |
| 6,977,323 | B1 | 12/2005 | Swenson |
| 6,979,324 | B2 | 12/2005 | Bybordi et al. |
| 6,987,209 | B2 | 1/2006 | Augustine et al. |
| 6,994,702 | B1 | 2/2006 | Johnson |
| 6,997,897 | B1 | 2/2006 | Silver et al. |
| 7,004,915 | B2 | 2/2006 | Boynton et al. |
| 7,008,400 | B2 | 3/2006 | Silver et al. |
| 7,022,113 | B2 | 4/2006 | Lockwood et al. |
| 7,067,709 | B2 * | 6/2006 | Murata et al. ................... 602/41 |
| 7,070,584 | B2 | 7/2006 | Johnson et al. |
| 7,077,832 | B2 | 7/2006 | Fleischmann |
| 7,087,806 | B2 * | 8/2006 | Scheinberg et al. ............ 602/41 |
| 7,108,683 | B2 | 9/2006 | Zamierowski |
| 7,117,869 | B2 | 10/2006 | Heaton et al. |
| 7,122,046 | B2 | 10/2006 | Augustine et al. |
| 7,128,735 | B2 | 10/2006 | Weston |
| 7,141,714 | B2 | 11/2006 | Nielsen |
| 7,195,624 | B2 | 3/2007 | Lockwood et al. |
| 7,214,202 | B1 | 5/2007 | Vogel et al. |

(56) References Cited

U.S. PATENT DOCUMENTS

| | | |
|---|---|---|
| 7,216,651 B2 | 5/2007 | Argenta et al. |
| 7,238,850 B2 | 7/2007 | Shimanuki |
| 7,255,681 B1 | 8/2007 | Silver et al. |
| 7,273,054 B2 | 9/2007 | Heaton et al. |
| 7,279,612 B1 | 10/2007 | Heaton et al. |
| 7,316,672 B1 | 1/2008 | Hunt et al. |
| 7,335,809 B2 | 2/2008 | Riesinger |
| 7,338,482 B2 | 3/2008 | Lockwood et al. |
| 7,361,184 B2 | 4/2008 | Joshi |
| 7,381,211 B2 | 6/2008 | Zamierowski |
| 7,381,859 B2 | 6/2008 | Hunt et al. |
| 7,438,705 B2 | 10/2008 | Karpowicz et al. |
| 7,485,112 B2 | 2/2009 | Karpowicz et al. |
| 7,494,482 B2 | 2/2009 | Orgill et al. |
| 7,503,910 B2 | 3/2009 | Adahan |
| 7,524,315 B2 | 4/2009 | Blott et al. |
| 7,534,240 B1 | 5/2009 | Johnson |
| 7,534,927 B2 | 5/2009 | Lockwood et al. |
| 7,569,742 B2 * | 8/2009 | Haggstrom et al. .......... 604/315 |
| 7,601,129 B2 | 10/2009 | Aali |
| 7,611,500 B1 | 11/2009 | Lina et al. |
| 7,615,036 B2 | 11/2009 | Joshi et al. |
| 7,625,362 B2 | 12/2009 | Boehringer |
| 7,645,269 B2 | 1/2010 | Zamierowski |
| 7,670,323 B2 | 3/2010 | Hunt et al. |
| 7,678,090 B2 | 3/2010 | Risk, Jr. et al. |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,722,582 B2 | 5/2010 | Lina et al. |
| 7,745,681 B1 | 6/2010 | Ferguson |
| 7,753,894 B2 | 7/2010 | Blott et al. |
| 7,754,936 B2 | 7/2010 | Heaton et al. |
| 7,758,514 B2 | 7/2010 | Grigoryants et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,803,980 B2 | 9/2010 | Griffiths et al. |
| 7,811,269 B2 | 10/2010 | Boynton et al. |
| 7,815,616 B2 | 10/2010 | Boehringer et al. |
| 7,816,577 B2 | 10/2010 | Aali |
| 7,828,782 B2 | 11/2010 | Suzuki |
| 7,838,716 B2 | 11/2010 | de Luis et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,858,838 B2 | 12/2010 | Holm et al. |
| 7,862,339 B2 | 1/2011 | Mulligan |
| 7,867,206 B2 | 1/2011 | Lockwood et al. |
| 7,880,050 B2 | 2/2011 | Robinson et al. |
| 7,884,258 B2 | 2/2011 | Boehringer et al. |
| 7,886,746 B2 | 2/2011 | Heaton et al. |
| 7,896,823 B2 | 3/2011 | Mangrum et al. |
| 7,896,856 B2 | 3/2011 | Petrosenko et al. |
| 7,909,805 B2 | 3/2011 | Weston |
| 7,910,791 B2 | 3/2011 | Coffey |
| 7,922,703 B2 | 4/2011 | Riesinger |
| 7,931,630 B2 | 4/2011 | Nishtala et al. |
| 7,951,100 B2 | 5/2011 | Hunt et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,976,519 B2 | 7/2011 | Bubb et al. |
| D642,594 S | 8/2011 | Mattson et al. |
| 7,988,680 B2 | 8/2011 | Lockwood et al. |
| 8,007,257 B2 | 8/2011 | Heaton et al. |
| 8,021,348 B2 | 9/2011 | Risk, Jr. et al. |
| 8,022,266 B2 | 9/2011 | Boehringer et al. |
| 8,025,650 B2 | 9/2011 | Anderson et al. |
| 8,062,272 B2 | 11/2011 | Weston |
| 8,062,273 B2 | 11/2011 | Weston |
| 8,092,441 B2 | 1/2012 | Sugito |
| 8,133,211 B2 | 3/2012 | Cavanaugh, II et al. |
| 8,158,844 B2 | 4/2012 | McNeil |
| 8,162,907 B2 | 4/2012 | Heagle |
| 8,211,071 B2 | 7/2012 | Mormino et al. |
| 8,215,929 B2 | 7/2012 | Shen et al. |
| 8,241,261 B2 | 8/2012 | Randolph et al. |
| 8,251,979 B2 | 8/2012 | Malhi |
| 8,257,328 B2 | 9/2012 | Augustine et al. |
| 8,282,611 B2 | 10/2012 | Weston |
| 8,303,552 B2 | 11/2012 | Weston |
| 8,308,714 B2 | 11/2012 | Weston et al. |
| 8,382,731 B2 | 2/2013 | Johannison |
| D679,819 S | 4/2013 | Peron |
| D679,820 S | 4/2013 | Peron |
| 8,569,566 B2 | 10/2013 | Blott et al. |
| 2001/0018602 A1 | 8/2001 | Augustine et al. |
| 2001/0029956 A1 | 10/2001 | Argenta |
| 2001/0031911 A1 | 10/2001 | Khouri |
| 2001/0034499 A1 | 10/2001 | Sessions et al. |
| 2001/0038799 A1 | 11/2001 | Silver et al. |
| 2001/0043943 A1 | 11/2001 | Coffey |
| 2002/0002209 A1 | 1/2002 | Mork |
| 2002/0017304 A1 | 2/2002 | Heaton et al. |
| 2002/0026133 A1 | 2/2002 | Augustine et al. |
| 2002/0065494 A1 | 5/2002 | Lockwood et al. |
| 2002/0082567 A1 | 6/2002 | Lockwood et al. |
| 2002/0143286 A1 | 10/2002 | Tumey |
| 2002/0150720 A1 | 10/2002 | Howard et al. |
| 2002/0161317 A1 | 10/2002 | Risk et al. |
| 2002/0161346 A1 | 10/2002 | Lockwood et al. |
| 2002/0183702 A1 | 12/2002 | Henley et al. |
| 2002/0198503 A1 | 12/2002 | Risk, Jr. et al. |
| 2002/0198504 A1 | 12/2002 | Risk, Jr. et al. |
| 2003/0014022 A1 | 1/2003 | Lockwood et al. |
| 2003/0021775 A1 | 1/2003 | Freeman |
| 2003/0023286 A1 | 1/2003 | Augustine et al. |
| 2003/0040687 A1 | 2/2003 | Boynton et al. |
| 2003/0045825 A1 | 3/2003 | Etheredge, III |
| 2003/0050594 A1 | 3/2003 | Zamierowski |
| 2003/0069529 A1 | 4/2003 | Augustine et al. |
| 2003/0069536 A1 | 4/2003 | Greter et al. |
| 2003/0069563 A1 | 4/2003 | Johnson |
| 2003/0088202 A1 * | 5/2003 | Gilman ......................... 602/46 |
| 2003/0125649 A1 | 7/2003 | Mcintosh et al. |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0188754 A1 | 10/2003 | Heaton et al. |
| 2003/0212357 A1 | 11/2003 | Pace |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2004/0006319 A1 | 1/2004 | Lina et al. |
| 2004/0019342 A1 | 1/2004 | Nagasuna et al. |
| 2004/0024351 A1 | 2/2004 | Greter et al. |
| 2004/0030304 A1 | 2/2004 | Hunt et al. |
| 2004/0039391 A1 | 2/2004 | Argenta et al. |
| 2004/0054338 A1 | 3/2004 | Bybordi et al. |
| 2004/0064111 A1 | 4/2004 | Lockwood et al. |
| 2004/0064132 A1 | 4/2004 | Boehringer et al. |
| 2004/0122434 A1 | 6/2004 | Argenta et al. |
| 2004/0127834 A1 | 7/2004 | Sigurjonsson et al. |
| 2004/0127862 A1 | 7/2004 | Bubb et al. |
| 2004/0127863 A1 | 7/2004 | Bubb et al. |
| 2004/0167482 A1 | 8/2004 | Watson |
| 2004/0171976 A1 | 9/2004 | Johnson |
| 2004/0225208 A1 | 11/2004 | Johnson |
| 2004/0241214 A1 | 12/2004 | Kirkwood et al. |
| 2004/0249353 A1 | 12/2004 | Risks, Jr. et al. |
| 2005/0004534 A1 | 1/2005 | Lockwood et al. |
| 2005/0010153 A1 | 1/2005 | Lockwood et al. |

(56) References Cited

U.S. PATENT DOCUMENTS

| | | |
|---|---|---|
| 2005/0020955 A1 | 1/2005 | Sanders et al. |
| 2005/0028828 A1 | 2/2005 | Heaton et al. |
| 2005/0070835 A1 | 3/2005 | Joshi |
| 2005/0070858 A1 | 3/2005 | Lockwood et al. |
| 2005/0080372 A1 | 4/2005 | Nielsen et al. |
| 2005/0085768 A1 | 4/2005 | Greter et al. |
| 2005/0090787 A1 | 4/2005 | Risk, Jr. et al. |
| 2005/0131327 A1 | 6/2005 | Lockwood et al. |
| 2005/0148913 A1 | 7/2005 | Weston |
| 2005/0165350 A1 | 7/2005 | Greter et al. |
| 2005/0177086 A1 | 8/2005 | Murata et al. |
| 2005/0203452 A1 | 9/2005 | Weston et al. |
| 2005/0222527 A1 | 10/2005 | Miller et al. |
| 2005/0222544 A1 | 10/2005 | Weston |
| 2005/0228329 A1 | 10/2005 | Boehringer et al. |
| 2005/0245850 A1 | 11/2005 | Freyre et al. |
| 2005/0261615 A1 | 11/2005 | Weston |
| 2005/0261643 A1 | 11/2005 | Bybordi et al. |
| 2005/0283105 A1 | 12/2005 | Heaton et al. |
| 2006/0009744 A1 | 1/2006 | Erdman et al. |
| 2006/0015087 A1 | 1/2006 | Risk, Jr. et al. |
| 2006/0025727 A1 | 2/2006 | Boehringer et al. |
| 2006/0029650 A1 | 2/2006 | Coffey |
| 2006/0041247 A1 | 2/2006 | Petrosenko et al. |
| 2006/0069365 A1 | 3/2006 | Sperl et al. |
| 2006/0070458 A1 | 4/2006 | Jones et al. |
| 2006/0079852 A1 | 4/2006 | Bubb et al. |
| 2006/0100594 A1 | 5/2006 | Adams et al. |
| 2006/0116620 A1 | 6/2006 | Oyaski |
| 2006/0149170 A1 | 7/2006 | Boynton et al. |
| 2006/0282028 A1 | 12/2006 | Howard et al. |
| 2007/0005028 A1 | 1/2007 | Risk, Jr. et al. |
| 2007/0021697 A1 | 1/2007 | Ginther et al. |
| 2007/0032762 A1 | 2/2007 | Vogel |
| 2007/0032778 A1 | 2/2007 | Heaton et al. |
| 2007/0038172 A1 | 2/2007 | Zamierowski |
| 2007/0055209 A1* | 3/2007 | Patel et al. ............ 604/315 |
| 2007/0078366 A1 | 4/2007 | Haggstrom et al. |
| 2007/0141128 A1 | 6/2007 | Blott et al. |
| 2007/0167927 A1 | 7/2007 | Hunt et al. |
| 2007/0185463 A1 | 8/2007 | Mulligan |
| 2007/0219513 A1 | 9/2007 | Lina et al. |
| 2007/0225663 A1* | 9/2007 | Watt et al. ............ 604/313 |
| 2007/0260207 A1 | 11/2007 | Ugander et al. |
| 2007/0265585 A1 | 11/2007 | Joshi et al. |
| 2007/0265586 A1 | 11/2007 | Joshi et al. |
| 2008/0004559 A1 | 1/2008 | Riesinger |
| 2008/0009812 A1 | 1/2008 | Riesinger |
| 2008/0033352 A1 | 2/2008 | Annis et al. |
| 2008/0039761 A1 | 2/2008 | Heaton et al. |
| 2008/0045887 A1 | 2/2008 | Larsson et al. |
| 2008/0082059 A1 | 4/2008 | Fink et al. |
| 2008/0108977 A1 | 5/2008 | Heaton et al. |
| 2008/0119802 A1 | 5/2008 | Riesinger |
| 2008/0167593 A1 | 7/2008 | Fleischmann |
| 2008/0177253 A1 | 7/2008 | Boehringer et al. |
| 2008/0200905 A1 | 8/2008 | Heaton et al. |
| 2008/0208147 A1 | 8/2008 | Argenta et al. |
| 2008/0223378 A1 | 9/2008 | Henderson et al. |
| 2008/0234641 A1 | 9/2008 | Locke et al. |
| 2008/0243044 A1 | 10/2008 | Hunt et al. |
| 2008/0294147 A1 | 11/2008 | Radl et al. |
| 2008/0306407 A1 | 12/2008 | Taylor |
| 2008/0306456 A1 | 12/2008 | Riesinger |
| 2008/0312572 A1 | 12/2008 | Riesinger |
| 2008/0312613 A1 | 12/2008 | Heaton et al. |
| 2009/0005746 A1 | 1/2009 | Nielsen et al. |
| 2009/0012483 A1 | 1/2009 | Blott et al. |
| 2009/0036873 A1 | 2/2009 | Nielsen et al. |
| 2009/0054855 A1 | 2/2009 | Blott et al. |
| 2009/0069759 A1 | 3/2009 | Blott et al. |
| 2009/0082740 A1 | 3/2009 | Lockwood et al. |
| 2009/0093779 A1 | 4/2009 | Riesinger |
| 2009/0131892 A1 | 5/2009 | Karpowicz et al. |
| 2009/0143753 A1 | 6/2009 | Blott et al. |
| 2009/0177135 A1 | 7/2009 | Rogers et al. |
| 2009/0192467 A1 | 7/2009 | Hansen et al. |
| 2009/0198201 A1 | 8/2009 | Adahan |
| 2009/0204084 A1 | 8/2009 | Blott et al. |
| 2009/0216170 A1 | 8/2009 | Robinson et al. |
| 2009/0216204 A1 | 8/2009 | Bhavaraju et al. |
| 2009/0221977 A1 | 9/2009 | Blott et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0254053 A1 | 10/2009 | Svensby et al. |
| 2009/0254066 A1 | 10/2009 | Heaton et al. |
| 2009/0259203 A1 | 10/2009 | Hu et al. |
| 2009/0264807 A1 | 10/2009 | Haggstrom et al. |
| 2009/0264837 A1 | 10/2009 | Adahan |
| 2009/0270820 A1 | 10/2009 | Johnson et al. |
| 2009/0287129 A1 | 11/2009 | Boehringer et al. |
| 2009/0293887 A1 | 12/2009 | Wilkes et al. |
| 2009/0299251 A1 | 12/2009 | Buan |
| 2009/0299255 A1 | 12/2009 | Kazala, Jr. et al. |
| 2009/0306580 A1 | 12/2009 | Blott et al. |
| 2009/0306609 A1 | 12/2009 | Blott et al. |
| 2009/0312723 A1 | 12/2009 | Blott et al. |
| 2010/0004611 A1 | 1/2010 | Aali |
| 2010/0016767 A1 | 1/2010 | Jones et al. |
| 2010/0022972 A1 | 1/2010 | Lina et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036334 A1 | 2/2010 | Heagle et al. |
| 2010/0042074 A1 | 2/2010 | Weston et al. |
| 2010/0063483 A1 | 3/2010 | Adahan |
| 2010/0069858 A1 | 3/2010 | Olson |
| 2010/0069863 A1 | 3/2010 | Olson |
| 2010/0087767 A1 | 4/2010 | McNeil |
| 2010/0100063 A1 | 4/2010 | Joshi et al. |
| 2010/0106112 A1 | 4/2010 | Vogel |
| 2010/0106117 A1 | 4/2010 | Lockwood et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0145289 A1 | 6/2010 | Lina et al. |
| 2010/0150991 A1 | 6/2010 | Bernstein |
| 2010/0159192 A1 | 6/2010 | Cotton |
| 2010/0160878 A1 | 6/2010 | Hunt et al. |
| 2010/0160880 A1 | 6/2010 | Weston |
| 2010/0174251 A1 | 7/2010 | Weston |
| 2010/0185163 A1 | 7/2010 | Heagle |
| 2010/0191196 A1 | 7/2010 | Heagle |
| 2010/0191198 A1 | 7/2010 | Heagle |
| 2010/0207768 A1 | 8/2010 | Pidgeon et al. |
| 2010/0210986 A1 | 8/2010 | Sanders et al. |
| 2010/0228205 A1 | 9/2010 | Hu et al. |
| 2010/0262090 A1 | 10/2010 | Riesinger |
| 2010/0262091 A1 | 10/2010 | Larsson |
| 2010/0268198 A1 | 10/2010 | Buan et al. |
| 2010/0278518 A1 | 11/2010 | Gordon |
| 2010/0280468 A1 | 11/2010 | Haggstrom et al. |
| 2010/0286635 A1 | 11/2010 | Watson, Jr. |
| 2010/0305490 A1 | 12/2010 | Coulthard et al. |
| 2010/0305526 A1 | 12/2010 | Robinson et al. |
| 2010/0318043 A1 | 12/2010 | Malhi et al. |
| 2010/0324510 A1 | 12/2010 | Andresen et al. |
| 2010/0331797 A1 | 12/2010 | Patel et al. |
| 2011/0004172 A1 | 1/2011 | Eckstein et al. |
| 2011/0004173 A1 | 1/2011 | Hu et al. |
| 2011/0015593 A1 | 1/2011 | Svedman et al. |
| 2011/0022013 A1 | 1/2011 | Boynton et al. |
| 2011/0028290 A1 | 2/2011 | Ozawa |
| 2011/0028919 A1 | 2/2011 | Johnnison et al. |
| 2011/0028920 A1 | 2/2011 | Johannison |
| 2011/0028921 A1 | 2/2011 | Hartwell et al. |
| 2011/0034869 A1 | 2/2011 | Greter et al. |
| 2011/0034888 A1 | 2/2011 | Aali |
| 2011/0034892 A1 | 2/2011 | Buan |
| 2011/0034894 A1 | 2/2011 | Riesinger |
| 2011/0046584 A1 | 2/2011 | Haggstrom et al. |

(56) References Cited

U.S. PATENT DOCUMENTS

| | | | |
|---|---|---|---|
| 2011/0046585 A1 | 2/2011 | Weston | |
| 2011/0054421 A1 | 3/2011 | Hartwell | |
| 2011/0054422 A1 | 3/2011 | Locke et al. | |
| 2011/0054423 A1 | 3/2011 | Blott et al. | |
| 2011/0087179 A2 | 4/2011 | Blott et al. | |
| 2011/0092927 A1 | 4/2011 | Wilkes et al. | |
| 2011/0092958 A1 | 4/2011 | Jacobs | |
| 2011/0105963 A1 | 5/2011 | Hu et al. | |
| 2011/0106030 A1 | 5/2011 | Scholz | |
| 2011/0112492 A1 | 5/2011 | Bharti et al. | |
| 2011/0118683 A1 | 5/2011 | Weston | |
| 2011/0125066 A1 | 5/2011 | Robinson et al. | |
| 2011/0130712 A1 | 6/2011 | Topaz | |
| 2011/0172615 A2 | 7/2011 | Greener | |
| 2011/0172617 A1 | 7/2011 | Riesinger | |
| 2011/0230849 A1 | 9/2011 | Coulthard | |
| 2011/0270201 A1 | 11/2011 | Bubb et al. | |
| 2011/0270202 A1 | 11/2011 | Boehringer et al. | |
| 2011/0282309 A1 | 11/2011 | Adie et al. | |
| 2011/0313373 A1 | 12/2011 | Riesinger | |
| 2011/0313374 A1 | 12/2011 | Lockwood et al. | |
| 2012/0041399 A1 | 2/2012 | Blott et al. | |
| 2012/0095380 A1 | 4/2012 | Gergeley et al. | |
| 2012/0109085 A1 | 5/2012 | McNeil | |
| 2012/0130332 A1 | 5/2012 | Cotton et al. | |
| 2012/0136325 A1 | 5/2012 | Allen et al. | |
| 2012/0157942 A1 | 6/2012 | Weston | |
| 2013/0110058 A1 | 5/2013 | Adie et al. | |
| 2013/0150814 A1 | 6/2013 | Buan | |
| 2013/0274688 A1 | 10/2013 | Weston | |

FOREIGN PATENT DOCUMENTS

| | | |
|---|---|---|
| DE | 3137839 A1 | 3/1983 |
| DE | 3935818 A1 | 5/1991 |
| DE | 4012232 A1 | 10/1991 |
| DE | 198 44 355 | 4/2000 |
| DE | 19844355 A1 | 4/2000 |
| EP | 0020662 B1 | 7/1984 |
| EP | 0355186 A1 | 2/1990 |
| EP | 0619105 A1 | 10/1994 |
| EP | 0777504 B1 | 10/1998 |
| EP | 1013290 A1 | 6/2000 |
| EP | 1411874 A1 | 7/2001 |
| EP | 1 726 276 | 11/2006 |
| EP | 1923077 B1 | 11/2006 |
| EP | 1880840 A1 | 1/2008 |
| EP | 1 985 270 | 10/2008 |
| EP | 1121163 B1 | 11/2008 |
| EP | 2185206 A2 | 1/2009 |
| EP | 2178573 A2 | 2/2009 |
| EP | 2098257 A1 | 9/2009 |
| EP | 1985270 A3 | 12/2009 |
| EP | 2326295 A1 | 3/2010 |
| EP | 2335749 A1 | 6/2011 |
| EP | 2349155 A2 | 8/2011 |
| EP | 1263366 B2 | 9/2011 |
| EP | 2420214 A1 | 2/2012 |
| FR | 1163907 A | 10/1958 |
| GB | 114754 | 4/1918 |
| GB | 236350 | 7/1925 |
| GB | 641061 | 8/1950 |
| GB | 1224009 A | 3/1971 |
| GB | 1400124 B | 7/1975 |
| GB | 1549756 A | 8/1979 |
| GB | 2195255 A | 4/1988 |
| GB | 2307180 A | 5/1997 |
| GB | 2378392 A | 2/2003 |
| GB | 2415908 A | 1/2006 |
| JP | 59-87824 | 6/1984 |
| JP | S61-80018 | 5/1986 |
| JP | 2003-165843 | 6/2003 |
| JP | 2005-334188 | 12/2005 |
| SU | 1251912 A1 | 4/1983 |
| WO | WO 84/01904 A1 | 5/1984 |
| WO | WO 90/11795 A1 | 10/1990 |
| WO | WO 91/00718 A1 | 1/1991 |
| WO | WO 92/20299 A2 | 11/1992 |
| WO | WO 96/05873 A1 | 2/1996 |
| WO | WO 99/01173 | 1/1999 |
| WO | WO 99/01173 A1 | 1/1999 |
| WO | WO 00/07653 A1 | 2/2000 |
| WO | WO 00/50143 A | 8/2000 |
| WO | WO 00/59424 A1 | 10/2000 |
| WO | WO 01/19430 A1 | 3/2001 |
| WO | WO 01/34223 A1 | 5/2001 |
| WO | WO 01/37922 A2 | 5/2001 |
| WO | WO 01/37922 A3 | 5/2001 |
| WO | WO 01/85248 A1 | 11/2001 |
| WO | WO 02/083046 A1 | 10/2002 |
| WO | WO 02/092783 A2 | 11/2002 |
| WO | WO 03/092620 A2 | 11/2003 |
| WO | WO 2004/024300 A1 | 3/2004 |
| WO | WO 2004/037334 | 5/2004 |
| WO | WO 2005/009488 A2 | 2/2005 |
| WO | WO 2005/016179 A2 | 2/2005 |
| WO | WO 2005/025666 A2 | 3/2005 |
| WO | WO 2005/046761 A1 | 5/2005 |
| WO | WO 2005/051461 A1 | 6/2005 |
| WO | WO 2005/070480 A1 | 8/2005 |
| WO | WO 2005/079718 | 9/2005 |
| WO | WO 2005/082435 A1 | 9/2005 |
| WO | WO 2005/105180 | 11/2005 |
| WO | WO 2005/123170 A1 | 12/2005 |
| WO | WO 2006/048246 A1 | 5/2006 |
| WO | WO 2006/052745 A2 | 5/2006 |
| WO | WO 2006/056294 A1 | 6/2006 |
| WO | WO 2006/081403 A1 | 8/2006 |
| WO | WO 2006/116992 A1 | 11/2006 |
| WO | WO 2007/002835 A2 | 1/2007 |
| WO | WO 2007/013064 A1 | 2/2007 |
| WO | WO 2007/019038 A2 | 2/2007 |
| WO | WO 2007/024230 | 3/2007 |
| WO | WO 2007/030598 A2 | 3/2007 |
| WO | WO 2007/030601 | 3/2007 |
| WO | WO 2007/084792 A2 | 7/2007 |
| WO | WO 2007/085396 A1 | 8/2007 |
| WO | WO 2007/106592 | 9/2007 |
| WO | WO 2007/106592 A2 | 9/2007 |
| WO | WO 2007/133618 A2 | 11/2007 |
| WO | WO 2008/013896 A2 | 1/2008 |
| WO | WO 2008/027449 A2 | 3/2008 |
| WO | WO 2008/040020 A2 | 4/2008 |
| WO | WO 2008/041926 A1 | 4/2008 |
| WO | WO 2008/100437 A1 | 8/2008 |
| WO | WO 2008/100440 A1 | 8/2008 |
| WO | WO 2008/112304 A1 | 9/2008 |
| WO | WO 2009/019227 A2 | 2/2009 |
| WO | WO 2009/019229 A2 | 2/2009 |
| WO | WO 2009/047524 A2 | 4/2009 |
| WO | WO 2009/062327 A1 | 5/2009 |
| WO | WO 2009/066105 | 5/2009 |
| WO | WO 2009/066106 | 5/2009 |
| WO | WO 2009/089390 | 7/2009 |
| WO | WO 2009/103031 | 8/2009 |
| WO | WO 2009/111657 | 9/2009 |
| WO | WO 2009/117635 A1 | 9/2009 |
| WO | WO 2009/122989 A1 | 10/2009 |
| WO | WO 2009/126833 | 10/2009 |
| WO | WO 2009/146441 | 12/2009 |
| WO | WO 2009/151380 | 12/2009 |
| WO | WO 2009/156709 A1 | 12/2009 |
| WO | WO 2009/158124 A1 | 12/2009 |
| WO | WO 2009/158130 A1 | 12/2009 |
| WO | WO 2010/026251 A1 | 3/2010 |
| WO | WO 2010/051418 A2 | 5/2010 |
| WO | WO 2010/072309 A1 | 7/2010 |
| WO | WO 2010/072395 A1 | 7/2010 |
| WO | WO 2010/120776 A1 | 10/2010 |
| WO | WO 2010/141271 A1 | 12/2010 |
| WO | WO 2010/147592 A1 | 12/2010 |

(56) References Cited

FOREIGN PATENT DOCUMENTS

| WO | WO 2011/019476 A1 | 2/2011 |
|----|-------------------|--------|
| WO | WO 2011/023275 A1 | 3/2011 |
| WO | WO 2012/022484    | 2/2012 |

OTHER PUBLICATIONS

Argenta, Louis C., et al., "Vacuum-Assisted Closure: A New Method for Wound Control and Treatment; Clinical Experience", Ann Plas Surg 1997;38:563-577 (Dec. 10, 1996).
Aubrey, D.A., et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Chariker, M.E., et al, "Effective Management of Incisional and Cutaneous Fistulae with Closed Suction Wound Drainage," Contemporary Surgery. Jun. 1989, pp. 59-63, vol. 34 USA.
Chintamani, et al., "Half versus full vacuum suction drainage after modified radical mastectomy for breast cancer—a prospective randomized clinical trial", Research Article (Jan. 27, 2005), 1-5.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
De Lange, M.Y., et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
Hartz, R.S., et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
Kalypto Medical, NPD 1000 Product Brochure (publication date unknown, believed to be Nov. 2010).
Kalypto Medical, NPD 1000 Negative Pressure Wound Care System, Clinician & Patient Instructions for Use (publication date unknown, believed to be Feb. 2010).
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirrgii, BlueSky Publishing, La Costa, California (2004), 3-4.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Canadian Office Action for Canadian Application No. 2739605 dated Aug. 22, 2011 in 2 pages.
International Search Report for PCT/GB2008/051088, mailed Mar. 4, 2009.
International Search Report for PCT/GB2008/051089, mailed Mar. 4, 2009.
NURSING75, Wound Suction: Better Drainage with Fewer Problems, Nursing, vol. 5, No. 10, Oct. 1975, pp. 52-55.
Prevena™ Incision Management System, Patient Guide, pp. 1-2, Jan. 2010.
Prevena™ Incision Management System, Clinician Guide, pp. 1-9, Jan. 2010.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).
Svedman, P., "Irrigation Treatment in Split-Thickness Skin Grafting of Intractable Leg Ulcers," Scand J. Plast. Reconst. Surg., 19:211-213, 1985.
Svedman, P., "Irrigation Treatment of Leg Ulcers," The Lancet, Sep. 1983, 532-34.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.
Swift, et al, "Quorum Sensing in Aeromonas hydrophila and Aeromonas salmoncida: Identification of LuxRI Homologs AhyRI and AsaRI and Their Cognate N-Acylhomoserine Lactone Signal Molecules," J. Bacteriol., 179(17):5271-5281 (1997).
Teder and Svedman et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-513, 1972 vol. 105.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applications of the Vacuum-Assisted Closure (VAC) Device", Am J Clin Dermatol (2005) 693, 185-194; Review Article (2005), 185-194.
Vijanto, J. and J. Raekallio, Local Hyperalimentation of Open Wounds, Br. J. surg., 1976, 63, 427-430.
Westaby, S., et al., "A Wound Irrigation Device", The Lancet, Sep. 2, 1978, pp. 503-504.
Webb, New Techniques in Wound Management: Vacuum-Assisted Wound Closure, Journal of the American Academy of Orthopaedic Surgeons, v. 10, No. 5, pp. 303-311, Sep. 2002.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
International Search Report for PCT/GB2008/051090 mailed Mar. 4, 2009.
Chinese First Office Action for Chinese Application No. 200880117222.4 dated Jul. 31, 2012 in 9 pages.
English Translation of First Office Action for Chinese Application No. 200880117222.4 dated Jul. 31, 2012 in 9 pages.
English Translation of Notice of Reasons for Rejection for Japanese Application No. 2010-534550 dated Nov. 13, 2012 in 4 pages.
Bragina, I.O., et al. "Russian Chemical Bulletin", Dec. 31, 1983.
Davydov, Y.A., et al., The Bacteriological & Cytological Assessment of Vacuum Therapy of Purulent Wounds, Vestnik Chirurgia 1988, October Edition 48-52 (in Russian with English translation). 1987.
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Webb, New Techniques in Wound Management: Vacuum-Assisted Wound Closure, Journal of the American Academy of Orthopadic Surgeons, v. 10, No. 5, pp. 303-311, Sep. 2002.
English Translation of First Chinese Office Action for Chinese Application No. 200880117352.8 dated Jul. 3, 2012 in 17 pages.
English Translation of First Chinese Office Action for Chinese Application No. 200880117224.3 dated Jul. 4, 2012 in 4 pages.
U.S. Appl. No. 13/912,716, filed Jun. 7, 2013, Joshi, et al.
US 6,216,701, 04/2001, Heaton et al. (withdrawn)
US 6,306,115, 10/2001, Kelly et al. (withdrawn)

\* cited by examiner

WOUND DRESSING

CROSS-REFERENCE TO RELATED APPLICATIONS

This application is a U.S. National Phase of the PCT International Application No. PCT/GB2008/051090 filed on Nov. 20, 2008, designating the United States and published on May 28, 2009 as WO 2009/066106, which claims priority to Great Britain Patent Application No. 0722820.8, filed Nov. 21, 2007, and Great Britain Patent Application No. 0817020.1, filed Sep. 17, 2008. The disclosure of these prior applications is incorporated by reference in their entirety and should be considered a part of this specification.

BACKGROUND OF THE INVENTION

Field of the Invention

The present invention relates to a method and apparatus for dressing a wound and a method for manufacturing a wound dressing. In particular, but not exclusively, the present invention relates to a wound dressing useable during topical negative pressure (TNP) therapy in which the wound dressing itself acts as a waste canister to collect and store wound exudate removed from a wound site.

There is much prior art available relating to the provision of apparatus and methods of use thereof for the application of topical negative pressure (TNP) therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In International patent application, WO 2004/037334, apparatus, a wound dressing and a method for aspirating, irrigating and cleansing wounds are described. In very general terms, the application describes the treatment of a wound by the application of TNP therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In International patent application, WO 2005104670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above-noted references is included herein by reference.

However, the above described apparatus and methods are generally only applicable to a patient when hospitalised as the apparatus used is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus. To this end GB-A-2 307 180 describes a portable TNP therapy unit which may be carried by a patient and clipped to belt or harness. A negative pressure can thus be applied at a wound site.

During TNP therapy a portable or non-portable therapy unit generates a negative pressure at a wound site. As fluid, including air as well as wound exudate material is removed from the wound site this must be collected in some manner remote from the wound site. With prior known therapy units the collection and storage of wound exudate material is typically carried out by a waste canister connected to a pump unit of the therapy unit. The use of a canister, however, can result in the therapy unit apparatus itself being quite bulky and expensive to manufacture. Also replacing a canister or a bag in a canister in which wound exudate is collected can be a time consuming and relatively unhygienic process.

Prior known therapy units also tend to include a pump which is used to generate the negative pressure. Such pumps can be costly to manufacture and are relatively heavy.

WO 2007/030601, which is incorporated herein by reference discloses a self-contained wound dressing with a micro pump. The pump for drawing wound fluid into a vacuum zone is included in a wound dressing itself. Nevertheless wound exudate from the dressing can only be removed via a complex series of steps. The exudate removal process is also prone to contamination since once an absorbent layer is fully saturated with wound exudate an access door must be opened in the wound dressing so that the absorbent layer and micro pump can be removed. It will be appreciated that such exudate removal and pump removal can be time consuming and can lead to cross contamination between users. A further problem is that the wound dressing is prone to over expansion and rupture.

SUMMARY OF SOME EXEMPLIFYING EMBODIMENTS

It is an aim of the present invention to at least partly mitigate the above-mentioned problems.

It is an aim of certain embodiments of the present invention to provide a method for providing negative pressure at a wound site to aid in wound closure and healing in which wound exudate drawn from a wound site during the therapy is collected and stored in a wound dressing.

It is an aim of certain embodiments of the present invention to provide a wound dressing which is able to be placed over a wound site and which includes an integrated pump to generate negative pressure at that wound site. Also for certain embodiments the wound dressing can collect any wound exudate.

According to a first aspect of the present invention there is provided apparatus for dressing a wound, comprising:
an absorbent layer for absorbing wound exudate;
a liquid impermeable, gas permeable filter layer over the absorbent layer; and
a cover layer comprising at least one orifice; wherein
the absorbent layer is in fluid communication with the filter layer.

According to a second aspect of the present invention there is provided a method of applying topical negative pressure (TNP) at a wound site, comprising the steps of:
pumping wound exudate and air from a wound site, a peripheral region around the wound site being sealed with a wound dressing;
collecting wound exudate, pumped from the wound site in an absorbent layer of the wound dressing; and
exhausting gas through at least one orifice in a cover layer of the wound dressing and a filter layer in fluid communication with the absorbent layer.

Certain embodiments of the present invention provide the advantage that a disposable wound dressing can be fixed over a wound site and can simultaneously be used to provide negative pressure at the wound site and collect and store wound exudate.

Certain embodiments of the present invention provide the advantage that a separate therapy unit is not required to generate negative pressure at a wound site and collect and store any wound exudate. Rather a wound dressing can carry out both a pumping and wound exudate collecting process. The wound dressing may then be a one use item which can be disposed of subsequent to use. This reduces a risk of contamination.

Certain embodiments of the present invention provide the advantage that a wound dressing can be used to collect wound exudate generated during a negative pressure therapy process. A pump remote from the wound dressing can be connected to the wound dressing and reused whilst the wound dressing itself is used to collect wound exudate and may then be disposed of after use.

BRIEF DESCRIPTION OF THE DRAWINGS

Embodiments of the present invention will now be described hereinafter, by way of example only, with reference to the accompanying drawings in which.

DETAILED DESCRIPTION OF SOME EXEMPLIFYING EMBODIMENTS

Figure 1:
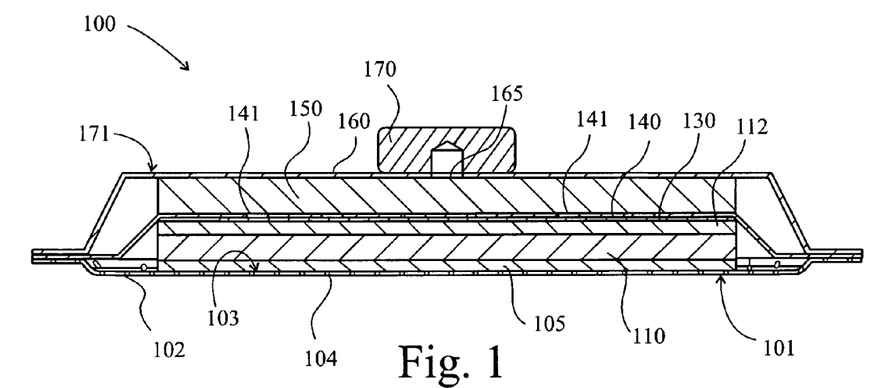
FIG. 1 illustrates a wound dressing.
Figure 2:
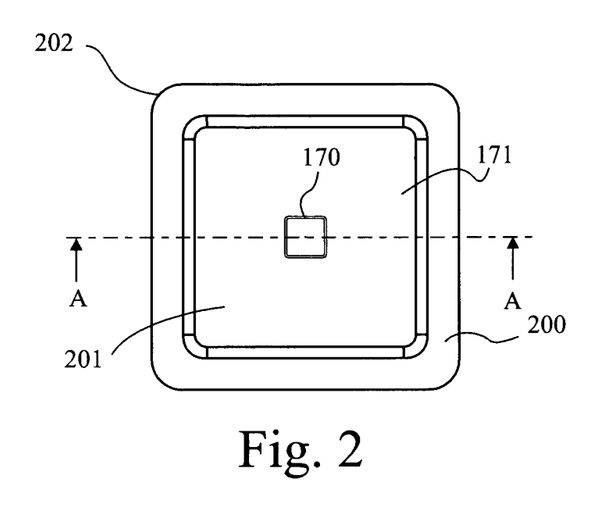
FIG. 2 illustrates a top view of a wound dressing.

FIG. 1 illustrates a cross section through a wound dressing 100 according to an embodiment of the present invention. A plan view from above of the wound dressing 100 is illustrated in FIG. 2 with the line A-A indicating the location of the cross section shown in FIG. 1. It will be understood that FIG. 1 illustrates a generalised schematic view of an apparatus 100.

It will be understood that embodiments of the present invention are generally applicable to use in topical negative pressure (TNP) systems. Briefly, negative pressure wound therapy assists in the closure and healing of many forms of "hard to heal" wounds by reducing tissue oedema; encouraging blood flow and granular tissue formation; removing excess exudate and reducing bacterial load (and thus infection risk). In addition, the therapy allows for less disturbance of a wound leading to more rapid healing.

The wound dressing 100 can be located over a wound site to be treated. The dressing 100 forms a sealed cavity over the wound site. Optionally wound packer can be used within a wound cavity below the dressing. Aptly the packer material can be a gauze or reticulated PU foam material.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

As illustrated in FIG. 1 a lower surface 101 of the wound dressing 100 is provided by an optional wound contact layer 102. The wound contact layer 102 can be a polyurethane layer or polyethylene layer or other flexible layer which is perforated, for example via a hot pin process or in some other way, or otherwise made permeable to liquid and gas. The wound contact layer has a lower surface 101 and an upper surface 103. The perforations 104 are through holes in the wound contact layer which enables fluid to flow through the layer. The wound contact layer helps prevent tissue ingrowth into the other material of the wound dressing. The perforations are small enough to meet this requirement but still allow fluid through. The wound contact layer also helps hold the whole wound dressing together and acts as a carrier for an optional lower and upper adhesive layer (not shown). For example, a lower pressure sensitive adhesive may be provided on the underside surface 101 of the wound dressing whilst an upper pressure sensitive adhesive layer may be provided on the upper surface 103 of the wound contact layer. The pressure sensitive adhesive which may be a silicone or acrylic based adhesive or other such adhesives may be formed on both sides or optionally on a selected one or none of the sides of the wound contact layer. When a lower pressure sensitive adhesive layer is utilised this helps adhere the wound dressing to the skin around a wound site.

An optional layer 105 of porous material such as a foam layer or the like is located above the wound contact layer. This porous layer allows transmission of fluid including liquid and gas away from a wound site into upper layers of the wound dressing. The layer 105 also helps distribute pressure generated by a pump, mentioned in more detail below, so that a whole wound site sees an equalised negative pressure. Reticulated foam or a non-woven material which might be natural or synthetic can be used as the porous material of the porous layer 105.

A layer 110 of absorbent material is provided above the transmission layer 105 or where no lower transmission layer is used on the wound contact layer or where no transmission layer 105 or wound contact layer 102 are used the absorbent layer lower surface forms the wound contact layer. The absorbent material which may be a foam or non-woven natural or synthetic material and which may optionally include or be super-absorbent material forms a reservoir for fluid, particularly liquid, removed from the wound site. The material of the absorbent layer also prevents liquid collected in the wound dressing from flowing in a sloshing manner. The absorbent layer 130 also helps distribute fluid throughout the layer via a wicking action so that fluid is drawn from the wound site and stored throughout the absorbent layer. This prevents agglomeration in areas of the absorbent layer. Since in use the absorbent layer experiences negative pressures the material of the absorbent layer is chosen to absorb liquid under such circumstances. Superabsorber material is an example of such a material. Non superabsorber material can be utilised however even where significant negative pressures are envisaged. The material of the absorbent layer does not need to be hydrophilic. Aptly a material with connective open voids can be used. Aptly a material is used that can resist the compressive force of the negative pressure e.g. precompressed FT11M foam manufactured by Foam Techniques. Aptly the absorbent material is selected so that fluid is prevented from draining back out when the dressing is removed. It is to be noted that if a superabsorber is used such a material is able to expand against the compressive force of the negative pressure.

A further optional layer 112 of porous material such as a foam layer or the like is located above the absorbent layer 110. This porous layer allows transmission of fluid including liquid and gas away from a wound site into upper layers of the wound dressing. The layer 112 also helps distribute pressure generated by a pump, mentioned in more detail below, so that a whole wound site sees an equalised negative pressure. Reticulated foam or a non-woven material which might be natural or synthetic can be used as a porous material of the porous layer 112. The material may the same or different from the previously mentioned layer 105 of porous material.

A filter layer 130 is provided over the absorbent layer 110. The filter layer permits moisture vapour and gas but no liquid through. A suitable material for the filter material of the filter layer 130 is 0.2 micron Gore™ expanded PTFE from the MMT range. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter.

It will be understood that other types of material could be used for the filter layer. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. Aptly the wound dressing 100 according to certain embodiments of the present invention uses microporous hydrophobic membranes (MHMs). Numerous polymers may be employed to form MHMs. For example, PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter layer 130 thus enables gas to be exhausted upwards through the wound dressing. Liquid, particulates and pathogens however are contained in the dressing.

A gas impermeable sealing layer 140 extends across the width of the wound dressing. The sealing layer which may, for example, be a polyurethane film having a pressure sensitive adhesive on both sides is impermeable to gas and this layer thus operates to seal a wound cavity over which the wound dressing is placed. In this way an effective chamber is made beneath the sealing layer and between the sealing layer and a wound site where a negative pressure can be established. The sealing layer 140 is sealed to the filter layer 130. For example via adhesive or welding techniques. Gas leaving the dressing thus passes through the filter layer and sealing layer.

Aptly the material of the sealing layer can have a high moisture vapour permeability for example Elastollan (Trade name) SP9109 manufactured by BASF. A dotted pattern spread acrylic adhesive can optionally be used to help improve moisture vapour permeability. An advantage of using a high moisture vapour permeability material as the sealing layer 160 is that the fluid handling capacity of the dressing may be increased significantly by the action of moisture transpiring through the film and dispersing into the atmosphere. Advantageously, transpiration rates can be easily achieved of the order of 3000 grams/centimeter square/24 hours as a result of the high humidity achieved in the dressing and intimate contact of material achieved during use of the apparatus at a negative pressure of up to 250 mmHg below atmospheric pressure.

As illustrated in FIG. 1 a grid array of through holes 141 are provided in the sealing layer. These enable fluid including gas and liquid to pass through the sealing layer 140. Alternatively where a separate cover layer and sealing layer are used the sealing layer may extend around only a circumferential area of the underlying layers where it seals between an outer layer (mentioned below in more detail) and the filter layer. As a result any gas leaving the wound site must leave via the filter layer. Liquid is retained in layers below the filter layer.

A layer 150 of porous material such as a foam layer or the like is located above the sealing layer 140. This porous layer allows transmission of fluid including liquid and gas away from a wound site. The layer 150 also helps distribute pressure generated by a pump, mentioned in more detail below, so that a whole wound site sees an equalised negative pressure. Reticulated foam or a non-woven material which might be natural or synthetic can be used as the porous material of the layer 150. The material may be the same or different from the material of the underlying layers 105, 112.

A cover layer 160 covers the absorbent layer of the wound dressing 100. The cover layer which, for example, may be a polyurethane film acts as a bacterial barrier and helps hold in liquid to stop fouling. The cover layer also provides integrity for the dressing and is impermeable to moisture vapour and gas. The cover layer helps hold the wound dressing together thus providing structural integrity. An upper surface 171 also presents a bacteria free non soiling surface. As an alternative the material of the cover layer can have a high moisture vapour permeability, for example Elastollan (Trade name) SP9109 manufactured by BASF. A dotted pattern spread acrylic adhesive can optionally be used to help improve moisture vapour permeability. An advantage of using a high moisture vapour permeability material as the cover layer 160 is that the fluid handling capacity of the dressing may be increased significantly by the action of moisture transpiring through the film and dispersing into the atmosphere. Advantageously, transpiration rates can be easily achieved of the order of 3000 grams/centimeter square/24 hours as a result of the high humidity achieved in the dressing and intimate contact of material achieved during use of the apparatus at a negative pressure of up to 250 mmHg below atmospheric pressure.

A single aperture 165 formed as a single hole or close arrangement of holes is formed in a central region of the upper cover layer. The aperture 165 is in fluid communication with an inlet to a pump 170 which is mounted on the upper surface 171 of the cover layer. In operation the pump 170 pumps fluid through the wound dressing from a wound site below the wound contact layer 102 upwards through the first transmission layer 105, absorbent layer 110, further transmission layer 112, filter layer 130, sealing layer 140, and further transmission layer 150.

Turning to FIG. 2 which illustrates a wound dressing 100 in accordance with an embodiment of the present invention one can see the upper surface 171 of the cover layer 170 which extends radially outwardly away from a centre of the dressing into a border region 200 surrounding a central raised region 201 overlying the foam layers and layer 110 of absorber. FIG. 2 also helps illustrate the location of the pump 170 on the cover layer. As indicated in FIG. 2 the general shape of the wound dressing is a square having equal side lengths with rounded corner regions 202. It will be appreciated that wound dressings according to other embodiments of the present invention can be shaped differently such as rectangular, circular or elliptical dressings.

Figure 3:
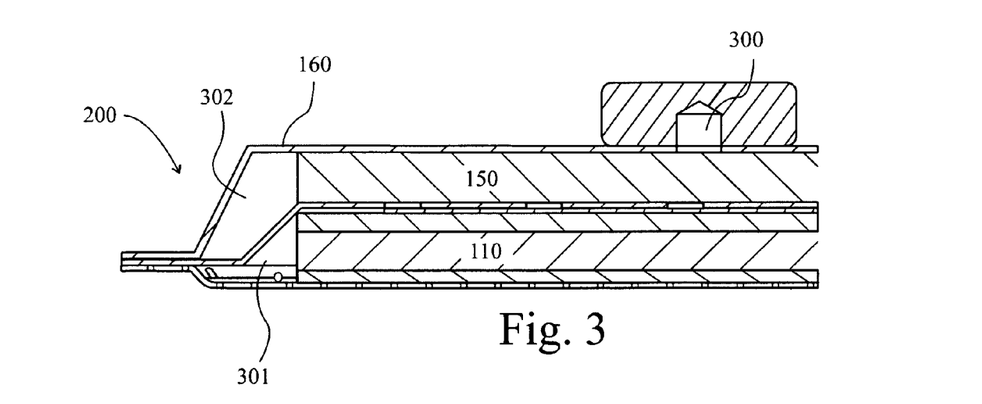
FIG. 3 illustrates a portion of the wound dressing.

FIG. 3 illustrates an expanded view of the border region 200 of the wound dressing 100 illustrated in FIGS. 1, 2 and 3. As seen, the cover layer 160 extends over the foam transmission layer 150 into an edge region. Here the cover layer is secured to the sealing layer 140 and the wound contact layer 102. FIG. 3 also helps illustrate how the perforations 104 in the wound contact layer 102 extend around the foam layer 105 and absorbent layer 110. It will be noted that a space 301 is indicated in FIG. 3 underneath the sealing layer 140 and above the wound contact layer 102 and ends of the transmission layers 105, 112 and absorbent layer 110. The space 301 is shown for illustrative reasons only and in practice the transmission layers and absorbent layers will be bevelled somewhat so as to reduce the space. A further space 302 is likewise illustrated in FIG. 3 above the sealing layer and below the inner surface of the cover layer. Again this is included for illustration only and in practice these spaces will be avoided due to a nipping process in the method of manufacture. It will also be appreciated by those skilled in the art that when put in use the wound dressing will be subject to a negative pressure within a region defined by the inner surface of the cover layer. Such a negative pressure will tend to collapse any remaining spaces.

It will be understood that according to embodiments of the present invention the wound contact layer is optional. This layer is, if used, porous to water and faces an underlying wound site. A lower porous layer 105 such as a reticulated PU foam layer is used to distribute gas and fluid removal such that all areas of a wound are subjected to equal pressure. The sealing layer together with the filter layer forms a substantially liquid tight seal over the wound. Thus as the pump 170 pumps a negative pressure is generated below the sealing layer. This negative pressure is thus experienced at the target wound site. Fluid including air and wound exudate is drawn through the wound contact layer and reticulated foam layer 105. The wound exudate drawn through the lower layers of the wound dressing is dissipated and absorbed into the absorbent layer where it is collected and stored. Air and moisture vapour is drawn upwards through the wound dressing through the intermediate transmission layer 112 and through the filter layer and sealing layer. The filter layer and sealing layer are secured together so as to prevent upward movement through the wound dressing of anything other than moisture vapour and air. This air and moisture vapour is drawn upwards by the pump 170 into the fluid inlet 300. The pump exhausts the fluid as air and moisture vapour through a fluid exit (not shown).

It is to be noted that the upper transmission layer 150 and cover layer 160 are optional. Their use is helpful during multi orientation use when portions of the filter layer might otherwise become occluded. When a separate cover layer 160 is not utilised the sealing layer also performs the extra function of covering the dressing and will thus additionally act as a cover layer.

It will be appreciated by those skilled in the art that rather than have a cover layer overlying the filter layer the cover layer may itself be overlain by a filter layer. The cover layer may thus be the outermost layer of the wound dressing or the filter layer may be the outermost layer of the wound dressing. Further outer layers (not shown) may optionally be used so long as they are gas and water vapour permeable.

As still further options the dressing can contain anti-microbial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilised. As a still further option odour trapping elements such as activated carbon, cyclodextrine, zealite or the like may be included in the absorbent layer or as a still further layer above the filter layer.

Figure 4:
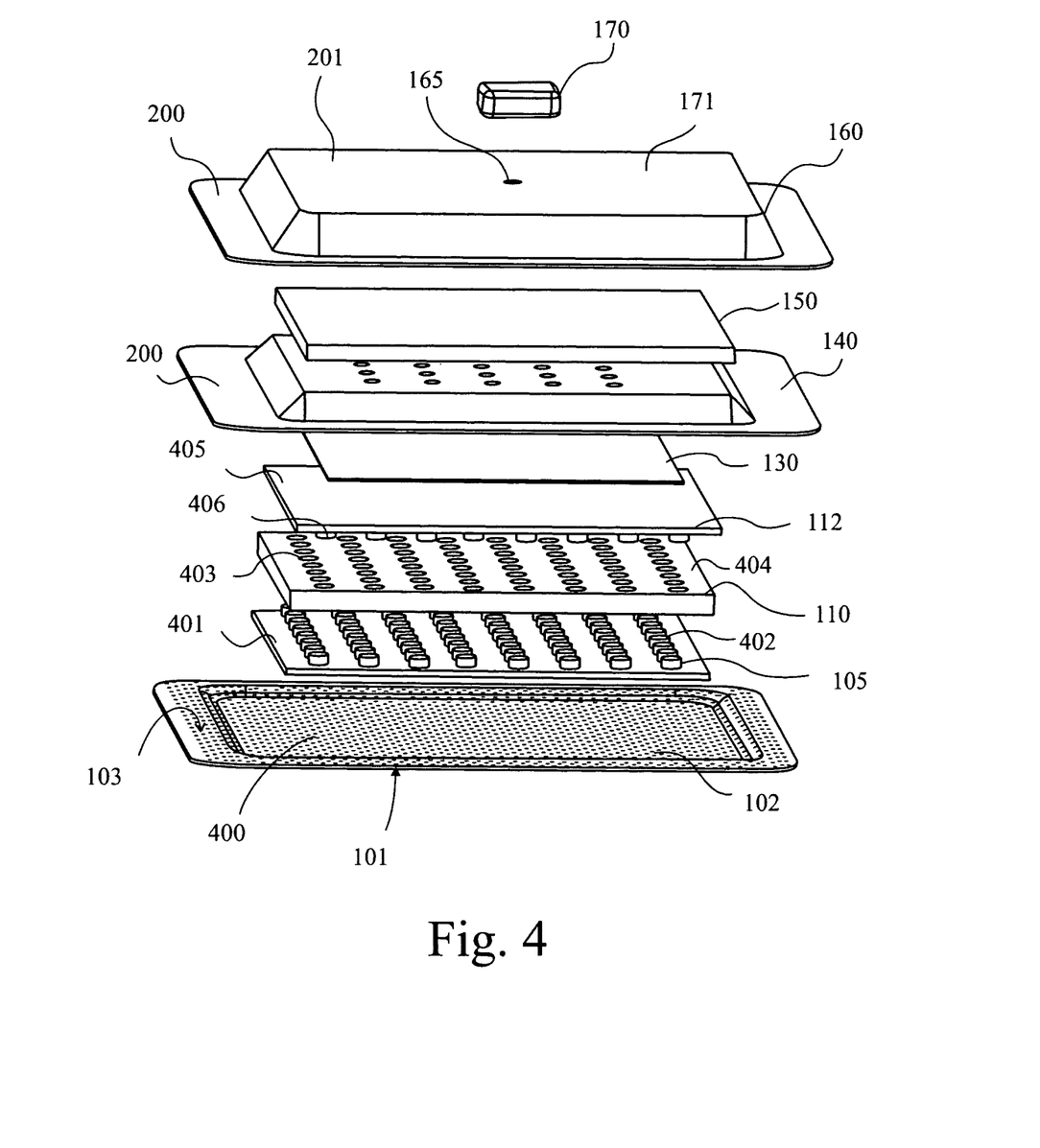
FIG. 4 illustrates an exploded view of a wound dressing with a mounted pump.

FIG. 4 illustrates an exploded view of the wound dressing illustrated in FIGS. 1, 2 and 3. As illustrated in FIG. 4 the lower-most layer of the wound dressing is a perforated wound contact layer 102. It will be appreciated that prior to use a still lower protective layer may be secured to the lower surface 101 of the wound contact layer. The protective paper (not shown) is removed immediately prior to application of the wound dressing over a wound site. During manufacture a central region 400 of the wound contact layer 102 is made slightly concave so as to provide a dished upper surface 103 for the wound contact layer.

A transmission layer 105 is duly located in the dished central region 400 of the wound contact layer. The foam layer includes a substantially rectangular base region 401 together with an array of upstanding columns 402. As illustrated in FIG. 4 an array of 8×8 columns 402 may be used. It will be appreciated that other numbers of columns may be utilised. The columns 402 have a substantially circular cross section although it will be appreciated that column elements having different cross section shapes could be used. The column elements 402 and base section 402 are aptly integrally formed although these could be separately formed with the column elements being secured to the base section in some appropriate way such as via adhesive techniques.

The absorbent layer 110 is located above the transmission layer 105. The absorbent layer 110 is a layer of absorbent material and includes through holes 403 formed in a substantially rectangular block 404 of absorbent material. The through holes are set out in an 8×8 array to coincide with the upstanding columns 402 in the underlying transmission layer.

It will be appreciated that the number and pattern of through bores 403 is selected to tally with the shape and number and arrangement of the columns.

The intermediate transmission layer 112 is a substantially rectangular base section 405 of porous material such as reticulated foam with an array of columns 406 extending downwardly from a lower surface of the base 405. The columns 406 coincide with locations of the through bores 403 in the absorbent layer. It will be appreciated that the columns 406 of the intermediate transmission layer 112 may be integrally formed with the base portion 405 of the transmission layer or may be secured in some fashion thereto. The height of the columns 402, 406 of the lower and intermediate transmission layers respectively is such that an upper contact surface of the columns 402 of the lower transmission layer and a lower contact surface of the columns 406 of the intermediate transmission layer contact when the wound dressing is put together. These thus provide fluid transmission paths through the absorber layer so that fluid, including air and wound exudate and liquid, is drawn from the lower region upwardly through the absorbent layer when the pump 170 is operating.

A rectangular layer of filter material 130 is located above the upper surface of the base section 405 of the intermediate transmission layer. The filter layer blocks movement therethrough of liquid. The filter layer is aptly a 0.2 micron Goren™ expanded PTFE sheet.

A sealing layer 140 is located over the filter layer 130. The sealing layer has a border region and a generally concave central region 407. The underside of the sealing layer 140 is thus recessed. An array of apertures set out in a 5×5 grid array is made through the sealing layer 140. The sealing layer away from the apertures is gas and fluid tight. If a material having a high moisture vapour permeability is optionally used then the sealing layer will of course be permeable to moisture vapour. Fluid, including liquid and gas, can of course penetrate through the perforations. The filter layer 130 which is secured on the underside of the sealing layer, however, prevents liquid penetration through the apertures and to an extent prevents penetration of air through the apertures. Moisture vapour can penetrate through the apertures.

An upper transmission layer formed as a sheet of reticulated foam is located over the central region of the upper surface of the sealing layer 140. The upper transmission layer acts as a manifold and diffuser to help spread the negative pressure generated by the pump 170.

A cover layer 160 is located over the sealing layer and upper transmission layer 150. The cover layer has a border region 200 and a central raised region 201. The underside of the cover layer thus presents a central dished region to receive the upper transmission layer, raised central region of the sealing layer and the filter layer, intermediate transmission layer, absorbent layer and lower transmission layer. A central aperture 165 is made in the centre of the upper surface of the cover layer. The central aperture 165 is located to coincide with a fluid inlet 300 of the pump 170. Thus in use when a pump 170 is in use a negative pressure is generated under the cover 160. This negative pressure is distributed throughout the wound dressing and at a target wound site located under the wound contact layer. As the negative pressure is established and maintained wound exudate and air is drawn upwards away from the wound site through the wound dressing. Liquid and air is drawn upwards through the wound contact layer into the base of the lower transmission layer 105 and upwards through the connecting columns in the lower transmission layer and intermediate transmission layer. It will be appreciated of course that columns having a height sufficient to bridge the whole of the absorbent layer could be provided on either the upper surface of the lower transmission layer 105 or the lower surface of the intermediate transmission layer 112. Alternatively the apertures 403 in the absorbent layer may be filled with transmissive material such as foam cylinders when the wound dressing is manufactured. Any wound exudate being drawn upward through the wound dressing is dissipated outwardly from the absorbent material in the aperture regions of the absorbent layer. The liquid is thus collected and stored in the absorbent layer. Air and moisture vapour carries on upwards through the filter layer 130 and sealing layer 140 and is evacuated by the pump 170.

Figure 5:
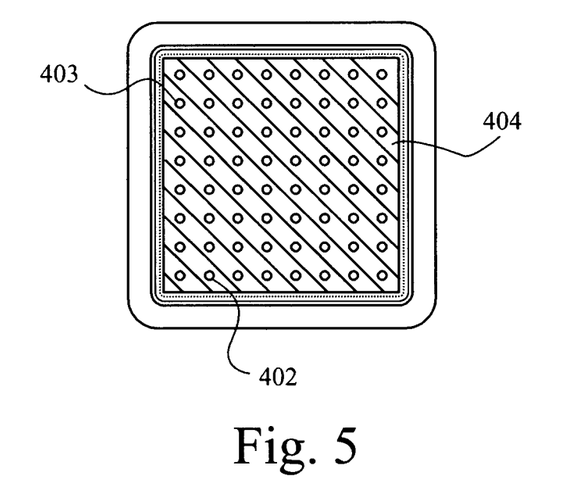
FIG. 5 illustrates a view of a horizontal section through a wound dressing.

FIG. 5 illustrates a horizontal cross section through the wound dressing illustrating an upper surface 404 of the absorbent layer including apertures 403. Each of the apertures 403 is filled with absorbent material such as columns 402 from the lower intermediate layer.

It will be appreciated that according to certain embodiments of the present invention fluid communication paths through which fluid can be transmitted from the lower transmission layer to the intermediate transmission layer can be made by pinching together peripheral regions of the lower and intermediate regions. Fluid transmission would thus proceed around the peripheral edges of the wound dressing. Such fluid paths may replace the fluid paths formed by the columns passing through apertures in the absorbent layer or may alternatively take the place of such passageways. This would maximise the quantity of absorber material in the layer 110 in the resultant wound dressing.

Figure 6:
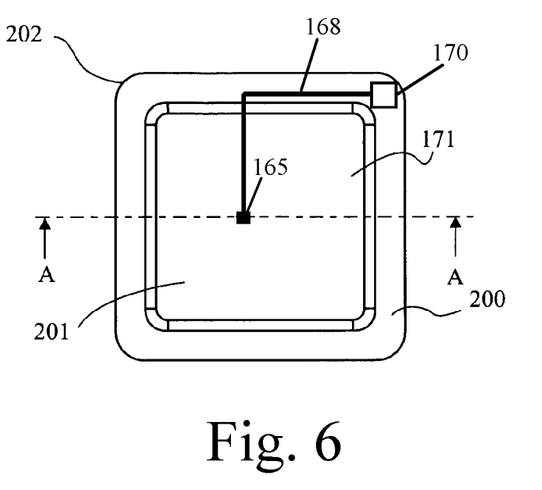
FIG. 6 illustrates a top view of a wound dressing.
In the drawings like reference numerals refer to like parts.

As illustrated in FIG. 6, it is to be noted that according to certain other embodiments of the present invention a remote pump 170 may be mounted to a border region 200 of the wound dressing rather than onto the top surface. In such case tubes 168 may be connected directly to the pump 170. Subsequent to a single use the wound dressing and pump may thus be discarded. As an option the tubes 168 may be provided with a click fit connector or other easy fit connector which can be connected to corresponding mating connectors joined via corresponding tubes to a remote pump 170. In this way a remote pump 170 may be reused whilst the wound dressing itself including connecting tubes and connectors is disposable after a single use.

It will be appreciated that alternatively the tubes could be provided by a single dual lumen tube. As a still further alternative the tubes may be provided by a single continuous looped tube, the tube then passing through pinch rollers for a peristaltic pump.

It will be understood that for embodiments of the present invention which include a pump mounted on the cover layer or on a peripheral border area of the dressing an integral power source and control circuitry can be included. Alternatively the power source can be external to the pump and remotely mounted. A remote power source and/or control circuitry improves the disposability of the dressing and permits battery recharge if spare batteries are used.

It is to be noted that in use the dressing may be used "up-side down", at an angle or vertical. References to upper and lower are thus used for explanation purposes only.

Where a separate cover layer and sealing layer are utilised such layers may be manufactured from the same or different materials.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. An apparatus for the treatment of a wound by applying negative pressure to the wound, the apparatus comprising:
   a wound contact layer comprising a plurality of perforations through the wound contact layer that allows for fluid to pass there through;
   a porous layer disposed over the wound contact layer configured to allow transmission of fluid away from a wound site and distribute negative pressure, through the wound contact layer, over the entire portion of the wound site being treated;
   an absorbent material configured to form a reservoir for fluid removed from the wound site, the absorbent material being disposed over the porous layer and comprising at least one substantially vertical through hole extending through the thickness of the absorbent material;
   a cover layer configured to cover the absorbent material; and
   a remote pump configured to apply negative pressure to the wound site through the perforations in the wound contact layer, through the porous layer, and through the at least one substantially vertical through hole and configured to draw fluid from the wound site into the absorbent material, the pump being connectable to the cover layer with at least one conduit;
   wherein the cover layer comprises at least one aperture configured to be in fluid communication with the pump, and wherein the aperture further comprises a gas permeable, liquid impermeable filter positioned thereat,
   wherein a portion of the porous layer extends through the at least one vertical through hole such that the portion of the porous layer contacts the filter when negative pressure is applied.

2. The apparatus of claim 1, wherein the wound contact layer comprises polyurethane and includes an adhesive.

3. The apparatus of claim 1, wherein the porous layer comprises a synthetic material.

4. The apparatus of claim 1, wherein the filter comprises a layer sealed to the cover layer.

5. The apparatus of claim 1, further comprising a wound packer material configured to be used within a wound cavity below the wound contact layer.

6. The apparatus of claim 1, wherein the cover layer is permeable to moisture vapor.

7. The apparatus of claim 1, wherein the cover layer comprises a polyurethane film and an adhesive.

8. The apparatus of claim 1, wherein the absorbent material comprises a synthetic superabsorbing material.

9. The apparatus of claim 1, wherein the wound contact layer, the porous layer, the absorbent material, and the cover layer form a wound dressing.

10. The apparatus of claim 1, wherein the cover layer comprises a plurality of holes.

11. The apparatus of claim 1, wherein the absorbent material comprises a plurality of through holes.

12. The apparatus of claim 1, further comprising a sealing layer disposed between the cover layer and the absorbent material.

13. The apparatus of claim 12, wherein the sealing layer comprises one or more through holes that permit gas and liquid to pass through.

14. The apparatus of claim 1, wherein the absorbent material is porous.

15. The apparatus of claim 1, wherein the porous layer disposed over the wound contact layer is configured to distribute negative pressure through the wound contact layer, equally over the entire portion of the wound site being treated.

16. The apparatus of claim 1, wherein the porous layer is provided directly over the plurality of perforations in the wound contact layer.

17. The apparatus of claim 1, wherein the porous layer comprises a reticulated material.

18. The apparatus of claim 1, wherein the porous layer comprises reticulated foam.

19. The apparatus of claim 1, wherein the porous layer comprises a non-woven material.

20. The apparatus of claim 1, wherein the wound contact layer comprises an upper surface and a lower surface, and further comprising an adhesive on the lower surface, wherein the adhesive is configured to adhere the wound contact layer to the wound.

21. An apparatus for the treatment of a wound by applying negative pressure to the wound, the apparatus comprising:
   a wound contact layer comprising a plurality of perforations through the wound contact layer that allows for fluid to pass there through;
   a porous layer disposed over the wound contact layer configured to allow transmission of fluid away from a wound site and distribute negative pressure, through the wound contact layer, over the entire portion of the wound site being treated;
   an absorbent material configured to form a reservoir for fluid removed from the wound site, the absorbent material being disposed over the porous layer;
   a cover layer configured to cover the absorbent material; and
   a remote negative pressure source connectable to the cover layer with at least one conduit and configured to apply negative pressure to the wound site through at least one fluid transmission path passing through the perforations in the wound contact layer, through the porous layer, and alongside at least one edge of the absorbent material to draw fluid through the perforations in the wound contact layer and through the porous layer into the absorbent material, wherein the at least one fluid transmission path provides a path for gas to pass through the perforations in the wound contact layer and through the porous layer to the negative pressure source while traversing the absorbent layer without flowing therethrough;
   wherein the cover layer comprises an aperture in fluid communication with the source of negative pressure, and wherein the aperture further comprises a gas permeable, liquid impermeable filter positioned thereat,
   wherein a portion of the porous layer extends upwardly along the at least one edge of the absorbent material such that the portion of the porous layer contacts the filter when negative pressure is applied.

22. The apparatus of claim 21, wherein the negative pressure source comprises a pump.

23. The apparatus of claim 21, further comprising a wound packer material configured to be placed within a wound site below the wound contact layer.

24. The apparatus of claim 21, wherein the absorbent material comprises a synthetic superabsorbing material.

25. The apparatus of claim 21, wherein the absorbent material comprises at least one through hole.

26. The apparatus of claim 21, wherein the at least one fluid transmission path alongside the at least one edge of the absorbent material comprises at least one through-hole in the absorbent material and the negative pressure is applied to the wound through the at least one through-hole.

27. The apparatus of claim 21, wherein the at least one fluid transmission path is alongside a peripheral edge of the absorbent material.

28. The apparatus of claim 21, wherein the wound contact layer, the porous layer, the absorbent material, and the cover layer form a wound dressing.

29. The apparatus of claim 21, further comprising a sealing layer disposed between the cover layer and the absorbent material.

30. The apparatus of claim 29, wherein the sealing layer comprises one or more through holes that permit gas and liquid to pass through.

31. The apparatus of claim 21, wherein the absorbent material is porous.

32. The apparatus of claim 21, wherein the porous layer disposed over the wound contact layer is configured to distribute negative pressure through the wound contact layer, equally over the entire portion of the wound site being treated.

33. The apparatus of claim 21, wherein the porous layer is provided directly over the plurality of perforations in the wound contact layer.

34. The apparatus of claim 21, wherein the porous layer comprises a reticulated material.

35. The apparatus of claim 21, wherein the porous layer comprises reticulated foam.

36. The apparatus of claim 21, wherein the porous layer comprises a non-woven material.

37. The apparatus of claim 21, wherein the wound contact layer comprises an upper surface and a lower surface, and further comprising an adhesive on the lower surface, wherein the adhesive is configured to adhere the wound contact layer to the wound.

* * * * *